United States Patent [19]

Vogel

[11] 4,030,490
[45] June 21, 1977

[54] FEMALE PROTECTIVE DEVICE

[76] Inventor: George N. Vogel, Box 705, Buzzards Bay, Mass. 02532

[22] Filed: Nov. 14, 1975

[21] Appl. No.: 631,811

[52] U.S. Cl. .............................................. 128/130
[51] Int. Cl.² ........................................... A61F 5/46
[58] Field of Search .......... 128/130, 1 R, 329, 215, 128/127, 131, 303

[56] References Cited
UNITED STATES PATENTS 3,039,468 6/1962 Price ................................. 128/347
3,675,639 7/1972 Cimber ............................. 128/1 R Primary Examiner—G.E. McNeill
Attorney, Agent, or Firm—Norman S. Blodgett; Gerry A. Blodgett

[57] ABSTRACT

Female protective device to prevent rape, the device including an elongated slender shaft having a sharp end, a first annular enlargement fixed around the shaft adjacent to but spaced from the sharp end, and a second enlargement connected by a flexible joint to the other end of the shaft. The device is worn internally with the sharp end pointed outwardly.

4 Claims, 3 Drawing Figures

FEMALE PROTECTIVE DEVICE

BACKGROUND OF THE INVENTION

One of the important accomplishments of the women's rights movement is the increased public attention being focused on the subject of rape. Thousands of rape cases are reported every year and the number is continuously rising. Perhaps even more important, however, is the recognition by the public that our system of justice and the psychological constraints imposed by our society have caused thousands more rapes per year to be unreported. While most women regard the possibility of being raped with a terror and a disgust bordering on psychosis, these feelings are almost equally strong against the possibility of being forced to publicly pursue conviction of the attacker. While the problem (and even the wide-spread public recognition of it) are by no means new, it appears that society is either unwilling or unable to cope with it. It appears, therefore, that, if rape prevention is to be accomplished, it must occur on the individual level.

Techniques which can be used by a potential rape victim to prevent the rape may be divided into active and passive methods. Active methods include weapons, unarmed self-defense techniques, and alarms. Weapons have numerous drawbacks which render them impractical in many situations. They require considerable skill and mental disposition in their use; they also open the door to substantial likelihood of self-injury when introduced into closequarter, physical-struggle type of contact. Furthermore, the carrying of various weapons is becoming progressively more regulated by government and such regulation may inevitably result in substantial legal liability even for justified use. Unarmed self-defense techniques, while appearing to provide a reasonable compromise in theory, have been found to be sadly deficient in practice. This is not only because they require the maintenance of a high level of skill and physical conditioning to be effective, but also they require a violent mental attitude in order to effectively eliminate an attacker, which attitude is alien to modern, law-abiding citizens. Various types of whistles and alarms that are intended to summon assistance are available on the market and can be effective in specific fact situations; they are not, however, a complete answer to the problem.

The concept of a passive prevention device which would make the rape impossible (and yet not require violent aggression by the victim) is much more consistent with practical realities. The expected violence involved in the attack, coupled with the ever-present threat, however, make the problem somewhat more difficult to solve than would appear at first glance. The standard solution has been a type of armored undergarment which could be locked in place to eliminate the possibility of rape. The problems involved in this concept become obvious when one considers that a device which is sufficiently strong and extensive to resist the efforts of the attacker is likely to pose substantial problems to everyday living. These and other difficulties experienced with the prior art devices have been obviated in a novel manner by the present invention.

It is, therefore, an outstanding object of the invention to provide an intravaginal device which will effectively prevent rape.

Another object of this invention is the provision of a device which is simple to manufacture, to fit to the individual user, and to use.

A further object of the present invention is the provision of a rape prevention device which will provide a maximum amount of security and protection at a minimum cost and inconvenience.

A still further object of the invention is the provision of a rape prevention device which is comfortable to wear and does not unduly restrict the physical activities of the wearer.

It is a further object of the invention to provide a rape prevention device of the passive type, that is to say, a device which carries out its function without the necessity for violent aggressive action by the user, so that the device is effective even when used by timid, frightened, or unconscious victims.

It is a further object of the invention to provide a rape prevention device which is inexpensive to manufacture and dispense.

It is another object of the invention to provide a rape prevention device that can be readily adjusted to the individual physical characteristics of the user.

With these and other objects in view, as will be apparent to those skilled in the art, the invention resides in the combination of parts set forth in the specification and covered by the claims appended hereto.

SUMMARY OF THE INVENTION

In general, the present invention involves an intravaginal protective device for frustrating a rape attempt, the device involving an elongated slender shaft having a first sharp end, a first enlargement concentrically fixed to the shaft adjacent to but shaped from the sharp end of the shaft, and a second enlargement fastened to the second end of the shaft by a flexible connection means. The device is worn in the vagina with the sharp end pointed outwardly, and the second enlargement located adjacent the cervix.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
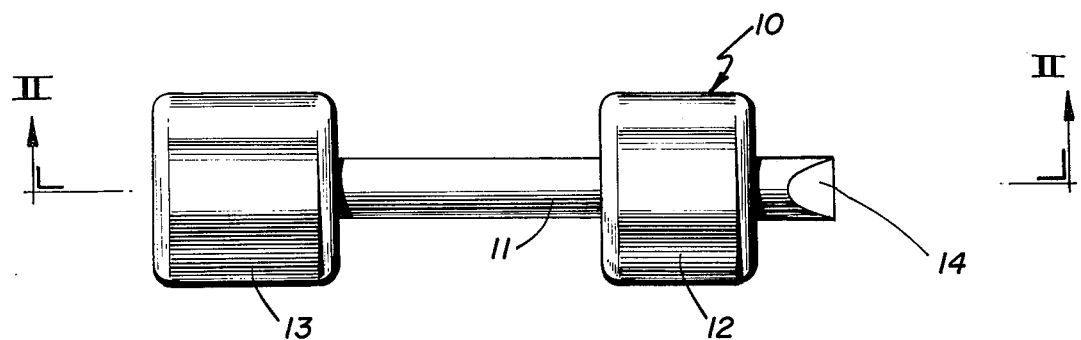
FIG. 1 is a side view of a device embodying the principles of the present invention.

Referring first to FIG. 1, in which are best shown the general features of the present invention, the device, indicated generally by the numeral 10, is shown to include an elongated shaft 11, a first engagement 12, and a second enlargement 13. The shaft 11 is a slender, elongated cylinder formed of a rigid plastic. One end 14 of the shaft 11 is truncated to form a relatively sharp edge at that end. The first enlargement 12 is generally cylindrical and is fixed to the shaft adjacent to but spaced from the first sharp end 14. The first enlargement 12 is concentric to the shaft, has a diameter of about 3 times the diameter of the shaft 11, and has a length approximately equal to its own diameter.

The second enlargement 13 is also cylindrical and is mounted on the second end of the shaft 11; it has the same general relative dimensions as the first enlargement.

Figure 2:
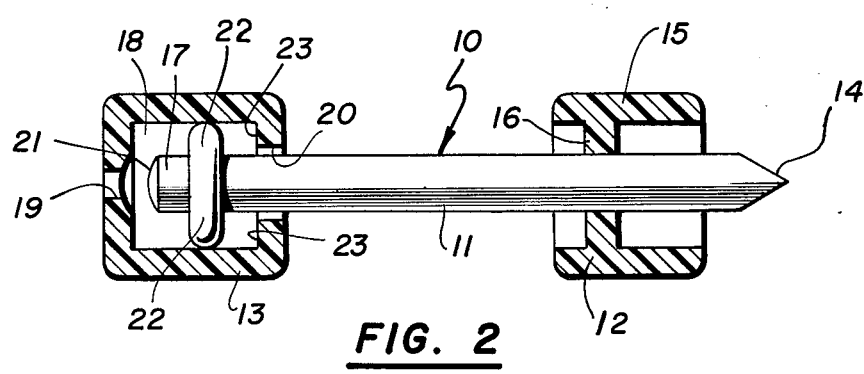
FIG. 2 is a sectional view taken along line II—II of FIG. 1.

Referring to FIG. 2, the sectional view of the device shows several of its other features. The first enlargement 12 actually is formed with an outer tubular wall 15 which is spaced from the shaft and with an axial integral web 16 which connects the wall to the shaft. This construction allows the enlargement 12 to be axially slidable on the shaft, for length adjustment, after which, said enlargement is fastened to shaft with adhesive. Surplus shaft is then cut off approximately one-half inch from the outer end of said enlargement and pointed.

The second enlargement 13 is attached to the second end of the shaft 17 by means of a universal joint. The enlargement 13, itself, has a cylindrical internal cavity 18, a small opening 19, and a large opening 20. The second end 17 of the shaft 11 has at its extreme, a hemispherical surface 21 which is of larger diameter than the small opening 19 which is a vent to prevent suction occurring at the time of removal. The shaft 11 passes through opening 20. The shaft also has an annular third enlargement 22 whose periphery lies outwardly of the shaft within the cavity 18 and engages an end 23 formed between the inner surface of the cavity 18 and the opening 20. This engagement attaches the second enlargement 13 to the end of the shaft, but allows universal motion of the enlargement with respect to the shaft. The device itself is constructed entirely of material which can be completely sanitizable using conventional methods. In the preferred embodiment, the device would be constructed of a rigid unbreakable plastic.

Figure 3:
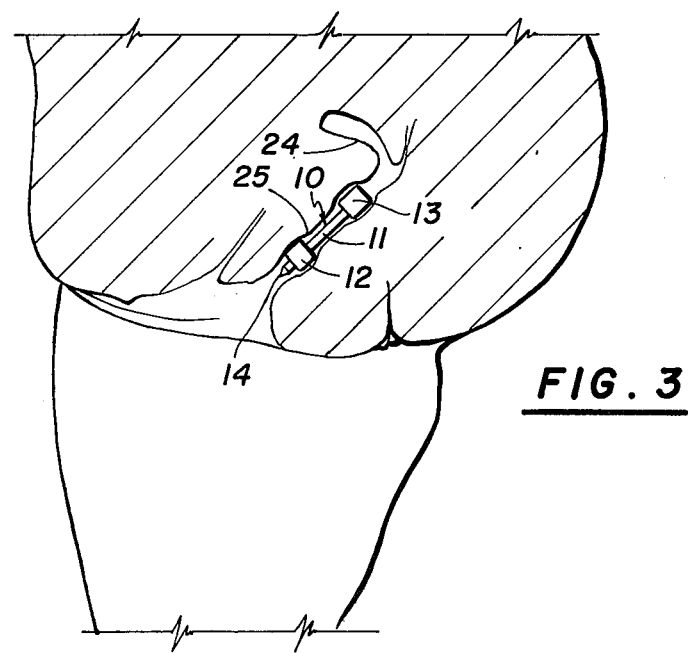
FIG. 3 is a sectional view of a female human body showing the device in use.

Referring to FIG. 3, the device 10 is shown as it would be normally worn by the user with the enlargement 13 located adjacent the cervix 24 and with the shaft 11 extending down the vagina 25 so that the pointed end 14 is slightly within the labia minor. The shaft itself could be supplied in a variety of sizes or could be cut to the proper size during fitting. The first enlargement 12 would be slid along the shaft until it rested in a comfortable position.

It has been found that, when the device of the present invention is properly designed and fitted, it can be worn comfortably and without danger during almost all normal activities. Thus, this device can be used on a semi-permanent basis or merely occasionally, depending on the desires of the user. When in use, the device essentially eliminates the possibility of penetration of the vagina by an attacker. While the device can be removed by the attacker, the process requires careful manipulation and cooperation from the victim, both of which are not consistent with the general rape context. It is suggested, furthermore, that the widespread and well-known use of this device would create a deterent effect far beyond the actual capability of the device because of the psychological factors that such a pointed instrument would generate. It is also suggested that use of the present device can provide psychologically a sense of security for those women who are terrorized by the potential dangers of rape in our modern world.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A female protection device comprising,
   a. an elongated slender shaft having a first sharp end and a second end,
   b. a first enlargement concentrically fixed to the shaft adjacent to but spaced from the sharp end of the shaft, and
   c. a second enlargement fixed to the second end of the shaft.

2. A device as recited in claim 1, wherein the second enlargement is mounted on the second end for substantial universal movement relative thereto.

3. A device as recited in claim 1, wherein the enlargements are of generally cylindrical shape and have equal diameters.

4. A device as recited in claim 1, wherein all parts of the device are made of a dense polymer that is easily cleaned.

* * * * *